United States Patent [19]

Rasmussen et al.

[11] Patent Number: 5,387,706
[45] Date of Patent: Feb. 7, 1995

[54] PROCESS FOR PREPARING ACYLOXYSILANES

[75] Inventors: Edward T. Rasmussen; Barbara A. Schroeder, both of Midland, Mich.; Monica A. Walker, Mill Valley, Calif.

[73] Assignee: Dow Corning Corporation, Midland, Mich.

[21] Appl. No.: 265,903

[22] Filed: Jun. 27, 1994

[51] Int. Cl.$^6$ .............................. C07F 7/08; C07F 7/09
[52] U.S. Cl. ...................................................... 556/442
[58] Field of Search .......................................... 556/442

[56] References Cited

U.S. PATENT DOCUMENTS

| | | | |
|---|---|---|---|
| 3,974,198 | 8/1976 | Ashby | 260/448.2 E |
| 4,176,130 | 11/1979 | John et al. | 260/448.2 E |
| 4,329,484 | 5/1982 | Petersen | 556/442 |
| 4,332,956 | 6/1982 | Tolentizio | 556/442 |
| 4,379,766 | 4/1983 | Mack et al. | 556/442 X |

*Primary Examiner*—Paul F. Shaver
*Attorney, Agent, or Firm*—William F. Boley

[57] ABSTRACT

A process for the preparation of acyloxysilanes. The process comprises contacting a chlorosilane with a carboxylic acid in a film forming an equilibrium mixture of acyloxysilane and hydrogen chloride. The film is heated at a temperature sufficient to cause vaporization of the hydrogen chloride from the equilibrium mixture thereby increasing the yield of acyloxysilane in the equilibrium mixture. In a preferred process, the process is run in a falling-film type reactor or a wiped-film type reactor.

13 Claims, No Drawings

PROCESS FOR PREPARING ACYLOXYSILANES

BACKGROUND OF INVENTION

The present invention is a process for the preparation of acyloxysilanes. The process comprises contacting a chlorosilane with a carboxylic acid in a film forming an equilibrium mixture of acyloxysilane and hydrogen chloride. The film is heated at a temperature sufficient to cause vaporization of the hydrogen chloride from the equilibrium mixture thereby increasing the yield of acyloxysilane in the equilibrium mixture. In a preferred process, the process is run in a falling-film type reactor or a wiped-film type reactor.

Acyloxysilanes are well known cross-linking agents for one-part room temperature vulcanizable silicone rubber compositions. Common acyloxysilane cross-linking agents include methyltriacetoxysilane and ethyltriacetoxysilane.

Acyloxysilane cross-linking agents have been made by the reaction of an appropriate chlorosilane with a carboxylic anhydride or with a carboxylic acid. The process is known to be an equilibrium reaction as described by the equation $$SiCl + AcOH \rightleftharpoons SiOAc + HCl,$$

where Ac is an acyl radical.

A reactive column distillation process for preparing acyloxysilanes by reacting a chlorosilane with a carboxylic acid or carboxylic acid anhydride in the presence of an iron complexing agent is disclosed in Ashby, U.S. Pat. No. 3,974,198, issued Aug. 10, 1976. Ashby describes a process where an aliphatic carboxylic acid, such as glacial acetic acid, is added at the top of a distilling column to a refluxing mixture of chlorosilane in an organic solvent, such as benzene, containing an iron complexing agent. After the completion of the addition of the aliphatic carboxylic acid, the solvent is removed by distillation, and the acyloxysilane compound is isolated from the mixture.

John et al., U.S. Pat. No. 4,176,130, issued Nov. 27, 1979, describe a reactive distillation column process where an aliphatic carboxylic acid in the vapor phase is passed upwards from the bottom of a column filled with Raschig rings countercurrent to a flow of chlorosilanes.

Tolentino, U.S. Pat. No. 4,332,956, issued Jun. 1, 1982, describes a reactive distillation column process where acyloxysilanes are prepared by reacting a chlorosilane with an aliphatic carboxylic acid in a column at an elevated temperature where the aliphatic carboxylic acid in the vapor phase reacts with the chlorosilane in the column. The improvement described by Tolentino comprises introducing the carboxylic acid into the column in a plurality of feed streams, where at least one feed stream of aliphatic carboxylic acid is located above the chlorosilane feed stream and one carboxylic acid feed stream below the chlorosilane feed stream.

In such reactive distillation processes as described above, the formation of dimer at the bottom of the column is a significant side reaction that results from thermal decomposition of monomeric acyloxysilanes or from a reaction of the chlorosilane with acyloxysilane or both. When this happens the yield of acyloxysilane product is reduced. Also, gels can form in the reactive distillation column causing plugging of the column. These detrimental processes are catalyzed by the presence of hydrogen chloride in the reaction mixture as well as by excess acetic acid.

The conduct of the reaction as a film process provides for good heat transfer to the film and good mass transfer thereby effecting rapid removal of hydrogen chloride from the reaction mixture. This results not only in a shifting of the equilibrium of the reaction to favor formation of the acyloxysilanes, but also a reduction in the undesired dimer formation catalyzed by the hydrogen chloride. In addition, the conduct of the reaction as a film process allows the use of lower reactor surface temperatures and shorter residence times than those required in reactive distillation columns. A reduction in reactor surface temperatures and residence times can reduce undesired side reactions, such as dimer formation and gelation.

SUMMARY OF INVENTION

The present invention is a process for the preparation of acyloxysilanes. The process comprises contacting a chlorosilane with a carboxylic acid in a film forming an equilibrium mixture of acyloxysilane and hydrogen chloride. The film is heated at a temperature sufficient to cause vaporization of the hydrogen chloride from the equilibrium mixture thereby increasing the yield of acyloxysilane in the equilibrium mixture. In a preferred process, the process is run in a falling-film type reactor or a wiped-film type reactor.

DESCRIPTION OF INVENTION

The present invention is a process for preparation of acyloxysilanes. The process comprises:

(A) contacting a chlorosilane described by formula $$R^1_a SiCl_{4-a} \qquad (1)$$

with a carboxylic acid described by formula $$R^2COOH \qquad (2)$$

in a film thereby forming an acyloxysilane and hydrogen chloride, (B) vaporizing the hydrogen chloride from the thin film to facilitate formation of the acyloxysilane, and (C) recovering the acyloxysilane;

where each $R^1$ is independently selected from a group consisting of hydrogen and monovalent hydrocarbon radicals comprising one to about eight carbon atoms, $R^2$ is selected from a group consisting of hydrogen atoms and alkyl radicals comprising one to about eight carbon atoms, and $a = 0$, 1, 2, or 3.

Chlorosilanes useful in the present process are described by formula (1), where each $R^1$ is independently selected from a group consisting of hydrogen and monovalent hydrocarbon radicals comprising one to about eight carbon atoms. In addition to hydrogen, $R^1$ may be the same or different substituted and unsubstituted monovalent hydrocarbon radicals comprising one to about eight carbon atoms. $R^1$ can be, for example, alkyl radicals such as methyl, ethyl, propyl, isopropyl, butyl, sec-butyl, octyl, and 2-ethylhexyl; alkenyl radicals such as vinyl and allyl; hexadienyl radicals; cycloalkyl radicals such as cyclopentyl, cyclohexyl, and cycloheptyl; aromatic hydrocarbon radicals such as phenyl and naphthyl; aralkyl radicals such as benzyl and phenylethyl; alkaryl radicals such as tolyl and dimethylphenyl; and substituted hydrocarbon radicals such as chloromethyl, 3-chloropropyl, and 3,3,3-trifluoropropyl.

In formula (1) it is preferred that a=1. Preferred chlorosilanes for use in the present process are selected from a group consisting of methyltrichlorosilane and ethyltrichlorosilane.

The chlorosilane of formula (1) is contacted with a carboxylic acid as described by formula (2). In formula (2) each $R^2$ is selected from a group consisting of hydrogen and alkyl radicals comprising one to eight carbon atoms. $R^2$ can be, for example, methyl, ethyl, propyl, tert-butyl, sec-butyl, and octyl. Preferred is when $R^2$ is methyl and the carboxylic acid is acetic acid.

The molar ratio of the carboxylic acid to silicon-bonded chlorine atoms of the chlorosilane in the thin film is not critical to the practice of the present process. However, it is preferred that the molar ratio of carboxylic acid to silicon bonded chlorine be within a range of about 40 to 200 percent of stoichiometric equivalence. More preferred is when the molar ratio of carboxylic acid to silicon bonded chlorine is about stoichiometric equivalence.

The chlorosilane and the carboxylic acid are contacted in a film. The term "film" is meant to include the coating or spreading of a bulk liquid onto a surface so as to increase the surface area of the bulk liquid and thereby increase mass transfer of components from the liquid to a vapor phase. The carboxylic acid, chlorosilane, or both may be preheated to a temperature below their boiling point prior to contact. The method of forming the film is not critical to the present process and can be any of those known in the art. The benefit of the present process is realized by the efficient transfer of heat and mass transfer within a film causing a rapid vaporization and removal of hydrogen chloride from the film. The vaporization and removal of hydrogen chloride from the film results in a shift of the chemical equilibrium of the reaction to favor production of acyloxysilanes. The film can be formed, for example, in a falling film evaporator-type reactor or in a wiped film evaporator-type reactor. Because of its simplicity of operation, a falling film evaporator-type reactor is generally preferred for conduct of the present process. Examples of such reactors are described, for example, in Kirk-Othmer, Encyclopedia of Chemical Technology, Fourth Edition, Vol. 9, p. 965–968, (1994); and in Mehra, "Selecting Evaporators," Chemical Engineering, Feb. 3, 1986, p. 56–72. The film forming reactor may be connected to a reboiler to facilitate conversion of lower-boiling materials exiting the reactor to higher-boiling materials within the reactor. The reactor may be used as a multiple pass reactor, where materials exiting the reactor are recycled to the reactor to effect further reaction of the materials.

Film thickness and flow rates will depend upon such factors as minimum wetting rate for the surface on which the thin film is formed and the flooding point. Standard methods for determining these parameters are described, for example, in Perry et al., Perry's Chemical Engineers' Handbook, 6th ed., McGraw-Hill, New York, p. 5–59; and in York et al., Chemical Engineering Progress, October 1992, p. 93–98.

Hydrogen chloride formed as a result of the contact of the chlorosilane with the carboxylic acid is vaporized from the film. Vaporization of the hydrogen chloride is effected by heating the thin film, by reducing pressure over the thin film, or by a combination of both. It is preferred that vaporization of the hydrogen chloride from the film be effected by heating the film. The film can be heated by standard methods, for example, passing a heated media such as a gas, water, or silicone oil through a jacket contacting the wall supporting the film. Generally, it is preferred that the temperature of the film be as great as possible without effecting significant vaporization of the chlorosilane fed to the reactor. For example, when the chlorosilane is methyltrichlorosilane a preferred temperature for a heating media provided to a jacketed reactor is about 85° C. to 100° C. and when the chlorosilane is ethyltrichlorosilane a preferred temperature for the heating media is about 95° C. to 115° C.

The hydrogen chloride vaporized from the present process is removed from the reactor by standard methods, for example, venting and can be collected and used as a feed to other processes.

Acyloxysilanes are recovered from the present process. The acyloxysilanes which can be recovered from the present process are described by reference to formula 1, where one or more of the chlorine substituents of the silicon atom of the chlorosilane is replaced by an acyloxy radical. Preferred acyloxysilanes prepared by the present process are methyltriacetoxysilane and ethyltriacetoxysilane.

Recovery of the acyloxysilanes from the present process may consist of simply retaining an acyloxysilane containing liquid mixture resulting from the contact of a chlorosilane with an acyloxysilane in a thin film. Recovery of the acyloxysilane can consist of using the acyloxysilane containing liquid mixture as a feed, for example, to a reactive distillation column to effect further reaction of the mixture. Recovery of the acyloxysilane can consist of standard separation processes, such as distillation, to further isolate the acyloxysilanes.

The following examples are provided to illustrate the present invention. These examples are not intended to limit the scope of the present claims.

EXAMPLE 1

The reaction of acetic acid with methyltrichlorosilane in a falling film evaporator-type reactor was evaluated. The reactor comprised a jacketed, glass, 2.5 cm internal diameter tube about 58 cm long. Syltherm TM heat exchange fluid, Dow Corning Corporation, Midland, Mich., was circulated through the reactor jacket at a temperature of about 95° C. A mixture comprising a 4.2:1 molar ratio (40 percent stoichiometric excess) of acetic acid and trichlorosilane was fed to the top of the reactor, where the mixture was distributed in a film by a 3.3 cm length wiper blade. The mixture was fed to the reactor at about 25 mL/min. The bottom fraction from the reactor was collected and passed through the reactor a total of seven passes. The product from the reactor was analyzed by gas chromatography using a thermal conductivity detector (GC-TCD). After seven passes, about 75 percent of the methyltrichlorosilane had been converted to acetoxysilanes and about 49 percent of the Added chlorine was removed as hydrogen chloride.

EXAMPLE 2

The effect of acetic acid concentration on the reaction with methyltrichorosilane in a falling-film evaporator type reactor was evaluated. The reactor and procedure was similar to that described in Example 1. The molar ratios of acetic acid to methyltrichlorosilane tested were: 2:1, 3:1, and 4.2:1. The bottom fraction from the reactor was passed through the reactor 5 times and then analyzed as described in Example 1. The fraction of methyltrichlorosilane converted to acetoxysilanes is reported in Table 1.

TABLE 1

Effects of Acetic Acid Concentration

| Molar Ratio | Methyltrichlorosilane Conv. |
|---|---|
| 2:1 | 0.51 |
| 3:1 | 0.64 |
| 5:1 | 0.73 |

EXAMPLE 3

The reaction of acetic acid with methyltrichlorosilane in a wiped film evaporator-type reactor connected to a reboiler was evaluated in a series of runs. The reactor comprised a 15 cm length jacketed, glass, tube with a 7.6 cm inside diameter. Syltherm heat exchange fluid was circulated through the reactor jacket at various temperatures between 65° C. and 96° C. A reboiler heated to 125° C was connected to the bottom of the reactor. A mixture comprising a 3:1 molar ratio of acetic acid to methyltrichlorosilane was fed to the top of the reactor. A wiped film of the mixture was formed in the reactor by means of three rotating teflon blades which extend the length of the reactor. The residence time of material in the reboiler was approximately 15 minutes. At the end of fifteen minutes the contents of the reboiler was analyzed by GC-TCD. A linear regression was performed on the results and calculated values for methylacetoxydichlorosilane (SiOAc), methyldiacetoxychlorosilane (SiOAc$_2$), and methyltriacetoxysilane (SiOAc$_3$), as reported in Table 2, were determined for various temperatures. The value for each of the acetoxysilanes is reported as the mole percent of methyltrichlorosilane converted to each of the acetoxysilanes. The estimated total conversion of methyltrichlorosilane to acetoxysilanes is reported in the column labelled "Total."

TABLE 2

Effects of Temperature on Acetoxysilane Yield

| Temp. °C. | Mole Fraction of Acetoxysilane | | | |
|---|---|---|---|---|
| | SiOAc | SiOAc$_2$ | SiOAc$_3$ | Total |
| 65 | 0.39 | 0.18 | 0.09 | 0.66 |
| 75 | 0.33 | 0.22 | 0.22 | 0.77 |
| 85 | 0.26 | 0.27 | 0.35 | 0.88 |
| 95 | 0.18 | 0.32 | 0.48 | 0.98 |

EXAMPLE 4

The effects of heat on dimer formation during the reaction of acetic acid with methyltrichlorosilane was evaluated using a wiped film evaporator-type reactor with and without a reboiler. The reactor was the same as in Example 3. The reactor was heated by passing Sytherm heat exchange fluid through the reactor jacket at a temperature of about 95° C. Feed to the reactor was a 3:1 molar mixture of acetic acid to methyltrichlorosilane. In a first run, a reboiler maintained at about 125° C. was used to reflux the bottom fraction coming off the wiped film evaporator-type reactor for a period of about 15 minutes. Conversion of methyltrichlorosilane to acetoxysilanes was about 95 percent with about 4 percent conversion to dimers. In a second run the bottoms coming off the reactor where collected in a flask and recycled through the reactor four times giving a total time in the reactor of about 15 minutes. The conversion of methyltrichlorosilane to acetoxysilanes was about 68 percent with about 2 percent conversion to dimers.

EXAMPLE 5

The reaction of acetic acid with ethyltrichlorosilane in a wiped film evaporator-type reactor connected to a reboiler was evaluated. The evaluation was conducted in the reactor described in Example 3. The reactor was heated by passing Sytherm heat exchange fluid through the reactor jacket at a temperature of about 94° C. The reboiler was maintained at a temperature of about 125° C. A 3:1 molar ratio of acetic acid to ethyltrichlorosilane was fed to the reactor. Resident time of material in the reboiler was about 15 minutes. At the end of 15 minutes the content of the reboiler was analyzed by GC-TCD. Conversion of ethyltrichlorosilane to acetoxysilanes was determined to be about 87 percent.

We claim:

1. A process for preparation of acyloxysilanes, the process comprising:

(A) contacting a chlorosilane described by formula

with a carboxylic acid described by formula

in a film thereby forming an acyloxysilane and hydrogen chloride, (B) vaporizing the hydrogen chloride from the film to facilitate formation of the acyloxysilane, and (C) recovering the acyloxysilane; where each $R^1$ is independently selected from a group consisting of hydrogen and monovalent hydrocarbon radicals comprising one to about eight carbon atoms, $R^2$ is selected from a group consisting of hydrogen and alkyl radicals comprising one to about eight carbon atoms, and a=0, 1, 2, or 3.

2. A process according to claim 1, were a=1.

3. A process according to claim 1, where the chlorosilane is selected from a group consisting of methyltrichlorosilane and ethyltrichlorosilane.

4. A process according to claim 1, where the carboxylic acid is acetic acid.

5. A process according to claim 1, where the molar ratio of carboxylic acid to silicon-bonded chlorine is within a range of about 60 to 200 percent of stoichiometric equivalence.

6. A process according to claim 1, where the molar ratio of carboxylic acid to silicon-bonded chlorine is about stoichiometric equivalence.

7. A process according to claim 1, where the film is formed in a falling-film evaporator type apparatus.

8. A process according to claim 1, where the film is formed in a wiped-film evaporator type apparatus.

9. A process according to claim 7, where the film exiting the apparatus is recycled to the reactor to effect further reaction.

10. A process according to claim 8, where the film exiting the apparatus is recycled to the reactor to effect further reaction.

11. A process according to claim 1, where vaporization of the hydrogen chloride from the film is effected by heating the film.

12. A process according to claim 1, where the acyloxysilane is selected from a group consisting of methyltriacetoxysilane and ethyltriacetoxysilane.

13. A process according to claim 1, where the chlorosilane is selected from a group consisting of methyltrichlorosilane and ethyltrichlorosilane, the carboxylic acid is acetic acid, the molar ratio of carboxylic acid to silicon-bonded chlorine is about stoichiometric equivalence, and the film is formed in a falling-film evaporator type apparatus.

* * * * *